United States Patent
Berg (10) Patent No.: US 7,319,399 B2
(45) Date of Patent: Jan. 15, 2008

(54) SYSTEM AND METHOD FOR MONITORING THE WEARING COMPLIANCE OF HEARING PROTECTION DEVICES

(75) Inventor: Christian Berg, Uerikon (CH)

(73) Assignee: Phonak AG, Staefa (CH)

(*) Notice: Subject to any disclaimer, the term of this patent is extended or adjusted under 35 U.S.C. 154(b) by 379 days.

(21) Appl. No.: 10/925,228

(22) Filed: Aug. 25, 2004

(65) Prior Publication Data

US 2006/0044140 A1 Mar. 2, 2006

(51) Int. Cl.
*G08B 23/00* (2006.01)
(52) U.S. Cl. .............. 340/573.1; 340/686.1; 181/135; 381/71.8; 381/312
(58) Field of Classification Search ........... 340/573.1, 340/540, 686.1, 686.2; 181/128, 130, 135; 128/864, 867; 2/208, 209; 381/312, 71.8
See application file for complete search history.

(56) References Cited

U.S. PATENT DOCUMENTS

| | | | | |
|---|---|---|---|---|
| 4,060,701 A | * | 11/1977 | Epley | 73/599 |
| 4,596,899 A | * | 6/1986 | Wojcik et al. | 379/52 |
| 5,317,273 A | * | 5/1994 | Hanson et al. | 324/616 |
| 5,426,719 A | * | 6/1995 | Franks et al. | 704/228 |
| 5,721,783 A | * | 2/1998 | Anderson | 381/328 |
| 6,438,245 B1 | * | 8/2002 | Taenzer et al. | 381/330 |
| 6,456,199 B1 | * | 9/2002 | Michael | 340/573.1 |
| 6,533,062 B1 | | 3/2003 | Widmer et al. | |
| 6,556,686 B1 | * | 4/2003 | Weidner | 381/312 |
| 6,603,860 B1 | * | 8/2003 | Taenzer et al. | 381/60 |
| 6,650,242 B2 | | 11/2003 | Clerk et al. | |
| 7,151,835 B2 | * | 12/2006 | Yonovitz et al. | 381/56 |
| 2003/0133583 A1 | | 7/2003 | Widmer et al. | |

FOREIGN PATENT DOCUMENTS

FR  2 658 586 A1  8/1991
WO  WO 99/66253 A1  12/1999

OTHER PUBLICATIONS

"Innovations report", Sep. 19, 2004, Präzise Ortung und Navigation im Zentimeterbereich, http://www.innovations-report.de\html\berichte\messenachrichten\bericht\17337.html.
Rowe, "UWB Applications in Siemens", Roke Manor Research 2002, UWB in Siemens, http://www.roke.co.uk/download/papers/uwb_applications_in_siemens.pdf.
K. Finkeneller, "Fundamental Operating Principles", *RFID Handbook: Fundamentals and Applications in Contactless Smart Cards and Identification*, 2nd Edition, Apr. 2003, John Wiley & Sons, Ltd.

* cited by examiner

*Primary Examiner*—Benjamin C. Lee
*Assistant Examiner*—Daniel Previl
(74) *Attorney, Agent, or Firm*—David S. Safran (57) ABSTRACT

A system for monitoring the use of a hearing protection unit comprising a left ear hearing protection device (14) and a right ear hearing protection device (12) to be worn by a user (10) within a monitoring area, an arrangement (16, 18, 22, 1006, 2006) for wirelessly detecting the position of the left ear hearing protection device (14) and the position of the right ear hearing protection device (12) within the monitoring area, a device (22) for judging whether a predefined condition for the detected positions of the left ear hearing protection device and the right ear hearing protection device is fulfilled, and a device (22) for outputting a wearing compliance signal depending on whether the predefined condition is found to be fulfilled by the judging device or not.

30 Claims, 3 Drawing Sheets

SYSTEM AND METHOD FOR MONITORING THE WEARING COMPLIANCE OF HEARING PROTECTION DEVICES

BACKGROUND OF THE INVENTION

1. Field of the Invention

The present invention relates to a system and method for monitoring the use of hearing protection devices to be worn by a user within a monitoring area. The invention further relates to detectable hearing devices and to a method for detecting the position of such hearing device.

2. Description of Related Art

A large part of the population is exposed to hazardous noise from time to time. This can be at work, whilst traveling, during leisure activities or at home. The exposure can lead to permanent hearing loss, distract people's attention from other hazards or simply cause stress. In order to prevent both accidents and permanent hearing damage, hearing protection devices (HPDs) have been provided in many styles and over many years. It started with the earmuff which is still very relevant and addresses very noisy environments (e.g. airports, construction, shooting) or complex working/communication situations (e.g. fighter pilots). Over the years development of biocompatible soft materials has enabled soft earplugs in different styles and colors as well as recent development of "one fits many" standard semi-soft earplugs in silicon-rubber type materials. For severe situations even the combination of an earmuff and an "in-the-ear" HPD is required to achieve desired attenuation. The physical limitation of hearing protection based on ear worn devices is defined where bone-conduction (body acoustics) becomes dominant at around 40 dB attenuation.

A common disadvantage of the above mentioned HPD styles is wearing discomfort. In case of the earmuffs, they are large which creates difficulties in combination with other head worn gear and they "close off" the ear too much for most applications. The in-the-ear styles mentioned are devices made to fit "the average" ear in one way or the other. Either the fit is provided by softness of the material which leads to undefined device insertion and undefined attenuation, or the fit is provided by standard shaped structures intended to block off the ear canal. In both cases the flat distribution of the individual shape of the outer ear and the ear canal leads to bad fit, pressure points in the ear and undefined positioning of the device.

To address this wearing comfort issue, in-the-ear hearing aid technology has been applied making customized ear molds with passive acoustical filter. These are long lasting devices with good wearing comfort. However, this customization process is traditionally a very manual process creating varying results over time, low reproducibility and the quality is very operator skill dependent.

The fabrication of customized shells by use of rapid prototyping technology, primarily for hearing aids, is described, for example, in U.S. Pat. No. 6,533,062 B1 or U.S. 2003/0133583 A1.

As already mentioned, hearing protection devices to be worn at the outer ear of the user, i.e. ear muffs, or to be worn at least in part within the user's ear canal, i.e. earplugs, are widely known. Both active devices, i.e. hearing protection devices comprising a microphone, a signal processing unit and a speaker for achieving selective sound attenuation, and passive devices, i.e. hearing protection devices without microphones and speakers, are used in practice. Hearing protection in general is of particular interest in industrial environments in order to protect the workers from hearing damages. While powerful hearing protection devices are available for such industrial environments, they will obviously not protect the worker, if he forgets or refuses to wear them in noisy environments. Hence, for achieving full hearing protection, it is not only necessary to develop appropriate hearing protection devices, but to also monitor the use of hearing protection devices in noisy environments, i.e. it would be desirable to provide for a control or monitoring of hearing protection device wearing compliance.

It is one object of the present invention to provide for a method and system for monitoring whether hearing protection devices are worn by a user within areas in which the use of hearing protection devices is required.

It is a further object of the invention to provide for a hearing device which can be identified or detected in a simple manner.

It is yet a further object of the invention to provide for a method for detecting such hearing devices, for example if lost.

SUMMARY OF THE INVENTION

The first object is achieved by a system and a corresponding method which involve detecting a position of a left ear hearing protection device and a position of a right ear hearing protection device within a monitoring area, judging whether a predefined condition for said detected positions of said left ear hearing protection device and said right ear hearing protection device is fulfilled, and outputting a wearing compliance signal depending on whether said predefined condition is found to be fulfilled.

This solution is beneficial in that it allows to monitor whether a user wears hearing protection devices within a given monitoring area. The generation of a wearing compliance signal may help to ensure that the hearing protection devices are actually worn by the user when required and may also serve to record the hearing protection device wearing compliance.

Having electromagnetic identification means, integrated within said hearing device, for providing, and adapted to provide, upon receipt of an electromagnetic input signal, an electromagnetic identification signal which is individual to said hearing device is beneficial in that such a hearing device can be detected if lost or may serve to identify the user wearing the hearing device. If designed as a hearing protection device, in addition it may serve to be used in a wearing compliance control system.

Receiving the identification signal and detecting the position of the passive hearing protection device from the received identification signal is beneficial in that it allows detection and identification of a hearing device, for example, if lost (e.g. in the food processing industry), or it may be used for a wearing compliance control system.

These and further objects, features and advantages of the present invention will become apparent from the following description when taken in connection with the accompanying drawings which, for purposes of illustration only, show several embodiments in accordance with the present invention.

Powerful hearing protection devices are available nowadays. In general, hearing protection devices include devices which are worn at the outer ear, i.e. ear muffs, and earplug devices, which are worn at least partly in the ear canal. In principle, hearing protection devices serve to attenuate the sound intensity which the ear of a user is exposed to, thereby protecting the user's ear from damages. Usually the sound attenuation function is provided by mechanical elements. Active hearing protection devices include, in addition to such mechanical attenuation elements, a microphone, an audio signal processing unit and a speaker so that the mechanical attenuation elements may be bypassed in order to make the sound attenuation selective, if, for example, the sound attenuation function is to be temporarily reduced or suspended in order to allow speech communication. Passive hearing protection devices do not include such additional electronic components. Unless otherwise specified, the present invention is intended to use all kinds of hearing protection devices.

However, hearing protection devices can only provide for the desired hearing protection function if worn by the user. Hence, in order to ensure that the user, for example, a worker in a noisy industrial environment, does not suffer from hearing damages, it is desirable to monitor the actual use of the hearing protection devices by the user in the areas in which such use is required.

Figure 1:
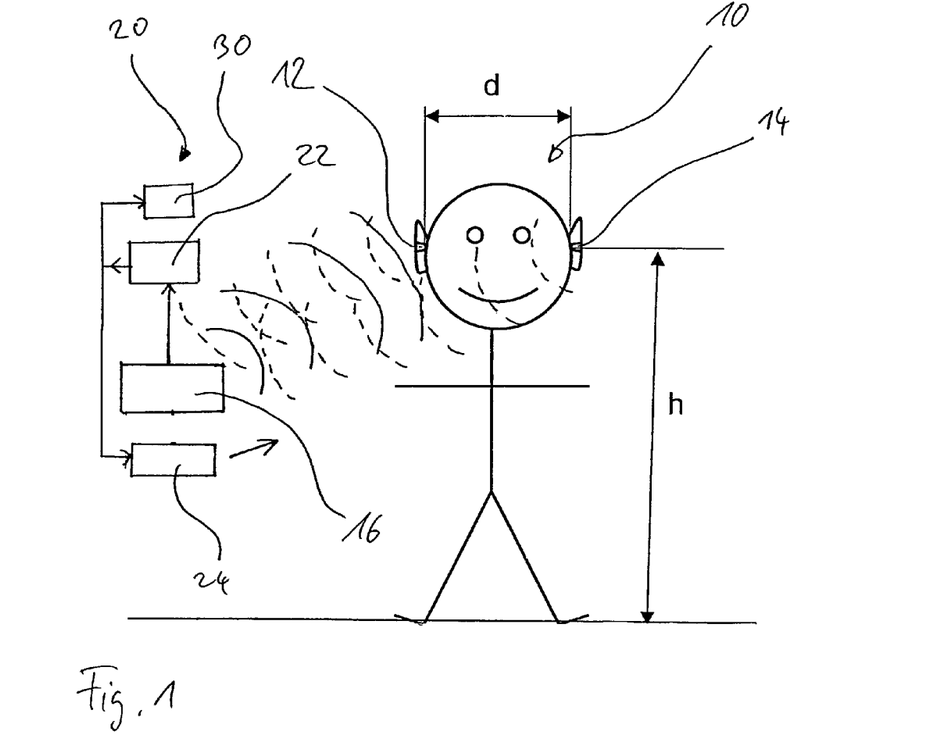
FIG. 1 shows a schematic example of a monitoring system for hearing protection wearing compliance.

FIG. 1 shows a schematic example of a system for monitoring the use of a hearing protection device in an area in which the use of hearing protection devices is required for the persons staying within this area.

In general, such a system requires means for detecting the position of the hearing protection devices within the monitoring area, means for judging whether a predefined spatial criterion for the detected positions of the hearing protection devices is fulfilled, and means for outputting a wearing compliance signal depending on whether this predefined spatial criterion is found to be fulfilled by the judging means or not. In addition, means may be provided for generating an optical or acoustic alarm signal from the wearing compliance signal, if the predefined spatial criterion is found to be not fulfilled.

Figure 2:
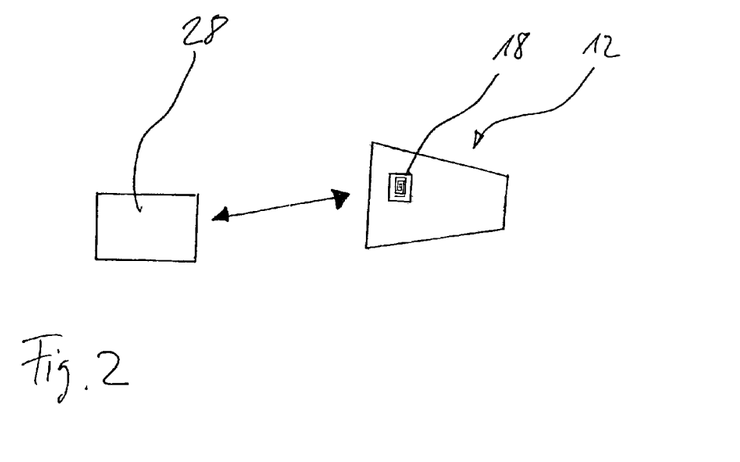
FIG. 2 shows a schematic view of a hearing protection earplug which may be used in the system of FIG. 1.

In the example shown in FIG. 1 a user 10 wears a hearing protection device 12 at his right ear and a hearing protection device 14 at his left ear. The monitoring system further comprises a unit 16 for transmitting and receiving electromagnetic signals which is located remote from the hearing protection devices 12, 14. According to FIG. 2, each hearing protection device 12, 14 includes a unit 18 which serves to respond to electromagnetic input signals transmitted by the remote transmitting receiving unit 16, in order to identify the respective hearing protection device 12, 14 and to enable detection of its position in space by the monitoring system 20.

The monitoring system 20 includes the electromagnetic signal transmitting/receiving unit 16, a control unit 22, an alarm unit 24 and a data log unit 30. In practice, at least two of the electromagnetic signal transmitting/receiving units 16 will be used spaced apart from each other in an appropriate manner in order to enable to detect the position of the hearing protection devices 12, 14 (in FIG. 1, only one of the units 16 is shown).

Figure 3:
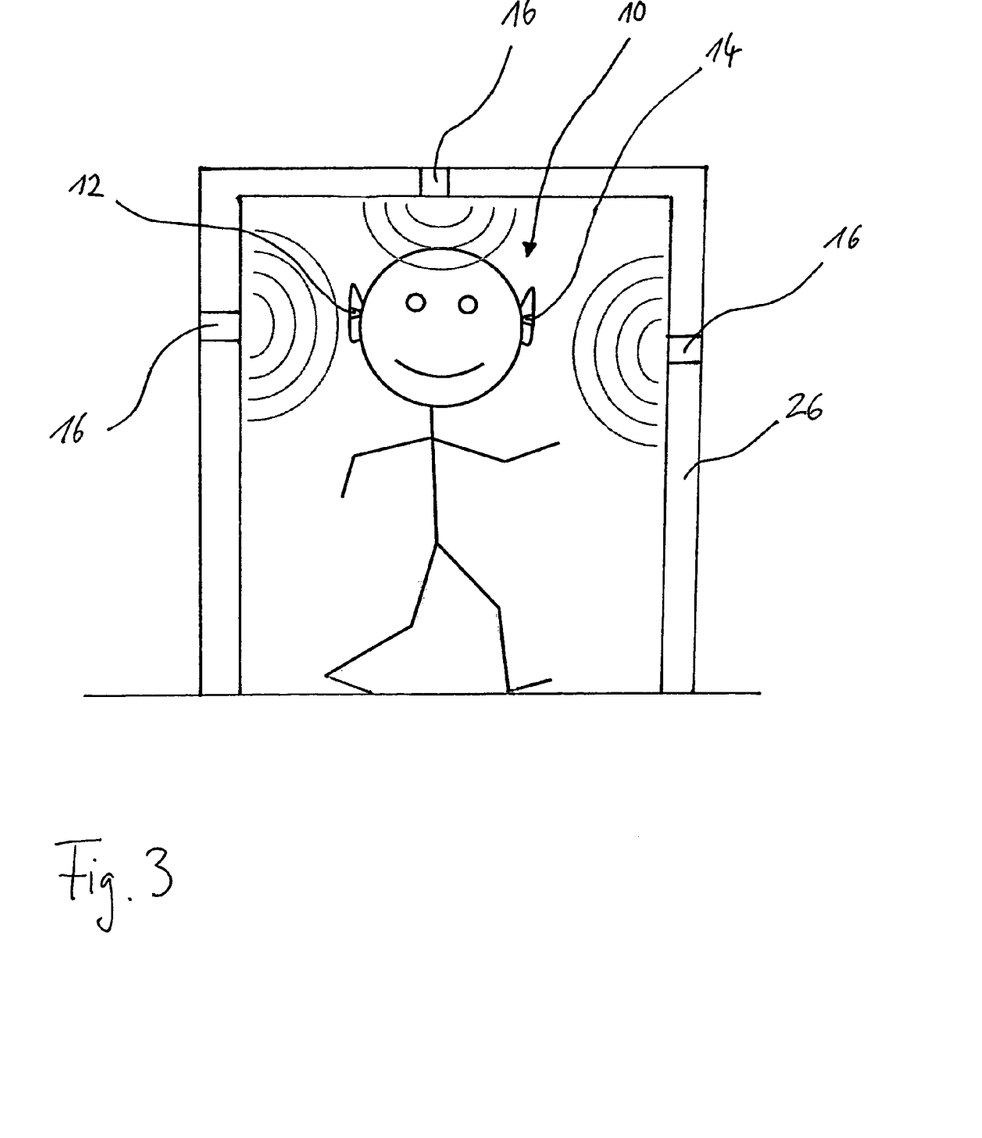
FIG. 3 shows another schematic example of a monitoring system for hearing protection wearing compliance.

FIG. 3 shows an arrangement wherein three of the electromagnetic signal transmitting/receiving units 16 are mounted at a frame 26.

In general, the three-dimensional detection of the position of an object by the use of electromagnetic signals, in particular radio frequency signals, is well known as such.

For example, at <http://www.innovations-report.de/html/berichte/messenachrichten/bericht-17337.html> a position detection system is described which allows for a precise three-dimensional (3D) localization of an active transponder with an accuracy of a few centimeters based on RF (radio frequency) FMCW (frequency modulated continuous wave) radar by using at least three spaced apart RF transmitter/receiver units which transmit a RF signal which is received, amplified, modulated and reflected by the transponder and then is mixed in each RF transmitter/receiver unit with the originally transmitted signal, whereby a signal is obtained which allows to determine the distance between the transponder and each RF transmitter/receiver unit, thus enabling to determine the 3D position of the transponder. At <http://www.multispectral.com/pdf/PAL2.pdf> a UWB (ultra wideband) localization system is described which comprises an active UWB tag and a plurality of UWB receivers, wherein the UWB tag emits nanosecond pulses for time-of-flight determination by the UWB receivers. A localization accuracy of 0.3 feet is reported. At <http://www.roke.co.uk/download/papers/uwb_applications_in_siemens.pdf> another UWB localization system is mentioned which allows for a localization accuracy of 1 cm for a tag-reader distance of 2 m and 2 cm for a distance of 20 m.

Preferably the monitoring system 20 operates at radio frequencies, i.e. the unit 16 transmits radio signals and also the response signals received from the response units 18 are radio frequency signals. Preferably, the response units 18 are designed as radio frequency identification tags (RFID-tags). RFID-tags as such are well-known and need not be discussed in detail here. A description of RFID-systems may be found, for example, in the "RFID-Handbook", $2^{nd}$ edition, by Klaus Finkenzeller, Wiley & Sons Ltd., April 2003.

In general, all kinds of RFID-tags may be used as the response unit 18 which are appropriate for the required distances between the hearing protection units 12, 14 and the transmitting/receiving units 16 (which, in practice, may range from several centimeters to several meters).

The response signal provided by the response unit 18 is different from the input signal transmitted by the signal transmitting/receiving units 16. Preferably the response unit 16 is adapted to be energized by energy included in the input signal received from the signal transmitting/receiving units 16 so that the response unit 18 does not need its own power source. Preferably, the response signal from the response 18 is specific to the individual hearing protection device 12, 14 so that each hearing protection device may be separately identified by the monitoring system 20. In this manner, also the user 10 may be identified, if each hearing protection device is assigned to a specific user by a corresponding implementation of the response unit 18. In order to achieve such user-specific assignment, the response unit 18 may be capable of being individually configured, preferably in a wireless manner, by a corresponding configuring unit 28. The configuring unit 28 may be implemented in a mobile device, such as personal computer, a personal digital assistant or a mobile phone. The response unit 18 comprises a non-volatile read/write data memory.

According to one embodiment, the response unit 18 comprises, in addition to a data memory, an antenna, an analogue circuit for receiving and transmitting radio frequency signals and a digital circuit for data processing. According to an alternative embodiment, the response unit 18 comprises an antenna, an analogue circuit for receiving and transmitting radio frequency signals and a surface acoustic wave device which acts as a read only data memory. In this case no digital circuit is necessary while nevertheless a digital response signal may be provided by the response unit 18. However, for this embodiment no remote programming of the response unit 18 is possible.

According to one embodiment, the signal transmitting/receiving units 16 and the response unit 18 are designed to be coupled inductively in order to energize the response unit 18 and to generate the response signal. The response signal may be actually transmitted by the antenna of the response unit 18 or it may serve to modulate the voltage in the resonance circuit of the signal transmitting/receiving units 18 via inductive coupling between the signal transmitting/receiving units 16 and the response unit 18.

According to an alternative embodiment, the signal response unit 18 may be designed for modulated reflection of the input signal from the signal transmitting/receiving units 16 in order to produce the response signal.

The data from the signal transmitting/receiving units 16 is collected in the control unit 22 for determining the position of the hearing protection device 12 and the position of the hearing protection device 14. The control unit 22 includes a module for judging whether the determined positions of the hearing protection units 12 and 14 fulfill a predefined spatial criterion for outputting a wearing compliance signal depending on whether the predefined criterion is found to be fulfilled or not.

In the most simple case, the spatial criterion could be that the detected vertical position of at least one of the hearing protection devices 12, 14 is within a predefined range. The centre value of this range would correspond to the average vertical level h of the hearing protection devices 12, 14 when correctly worn by the user, with the lower and upper limit of the range being selected according to the estimated measurement errors and the estimated fluctuations of the vertical level of the hearing protection devices 12, 14 due to the movements of the user.

A better result is achieved, if the vertical position of both hearing protection devices 12, 14 is considered and it is requested that both values are within the corresponding range. Alternatively, one might consider the mean of the vertical positions of both hearing protection devices 12, 14. As a further alternative, one might consider the difference of the vertical positions of the left ear hearing protection device 14 and the right ear hearing protection device 12 (for correct use, this difference should be close to zero).

Another option for the spatial criterion is to consider the distance between the detected position of the left ear hearing protection device 14 and the right ear hearing protection device 12, which, if the hearing protection devices 12, 14 are correctly worn, should correspond to about the distance d between the two ears of the user 10.

In most cases, the above discussed measures will have statistical uncorrelated spread so that a more reliable judgment could be achieved, if at least two of these measures are considered in combination. For example, one may take as the spatial criterion that the mean of the vertical positions of the hearing protection devices 12, 14 and the distance between the hearing protection devices 12, 14 are both within a respective predefined range, the center value of which corresponds to the height h of the user's ears above ground level and the distance d between the user's ears, respectively.

If the predefined spatial criterion is found to be not fulfilled (for example, if the distance or the vertical level of the detected positions of the hearing protection devices 12, 14 is outside the predefined respective range), the judgment module comes to the conclusion that the hearing protection devices 12, 14 are not properly worn by the user 10. In this case, a corresponding wearing compliance signal is output to the alarm unit 24 and the wearing log unit 30. The wearing log unit 30 serves to record the times when the hearing protection devices 12, 15 are not properly worn by the user 10. The alarm unit 24 will create an optical or acoustic alarm signal which can be perceived by the user 10.

Preferably the monitoring system 20 includes means for determining when the user enters or exits the monitoring area. This function may be provided by the detection of the presence of the response unit 18 within the monitoring area. According to one embodiment, the monitoring system 20 may be designed such that the position of the hearing protection devices 12, 14 is monitored over the entire period of time when the user is determined to be within the monitoring area.

According to an alternative embodiment, the monitoring system 20 is designed to determine when the user is at a predetermined location within the monitoring area. This function may be achieved by detecting the position of the response units 18. In this embodiment, the monitoring system 20 is designed to monitor the wearing of the hearing protection devices by the user only at the time when the user is determined to be at the predetermined location within the monitoring area. In other words, in this case the user is not monitored all the time he stays within the monitoring area, but only at one or more predetermined locations, for example, when he enters the monitoring area. An example for such an embodiment is shown in FIG. 3, wherein the signal transmitting/receiving units 16 are located at the frame 26 which might constitute the access gate to the monitoring area.

According to a preferred embodiment, the hearing protection device is a customized earplug to be worn at least in part in the user's ear canal, i.e. an earplug having a hard shell having an outer surface which is individually shaped according to the inner shape of the user's ear canal and outer ear measured for example by 3D laser scanning of the ear or by taking an impression of the ear which undergoes 3D laser scanning. In this case, the response unit 18 preferably is designed as a closed unit which is to be inserted into a cavity formed within the hard shell during the manufacturing process of the hard shell. The customized hard shell may be produced by an additive build-up process, for example by layer-by-layer laser sintering ("selective laser sintering") from a powder material, for example a polyamide powder material. The hard shell preferably has an elasticity from shore D 85 to shore D 65. Such processes are described, for example in U.S. Pat. No. 6,533,062 B1 or U.S. 2003/0133583 A1.

In this case, the feature of heaving a signal response unit 18 integrated within the hard shell of the customized earplug is an ordering option for the client which has to be entered into the work order for the customized earplug. Once in the production process, the response unit 18 will be programmed with the individual response signal in order to assign the earplug to the specific user. Such programming (i.e. individualization) of the response unit 18 can be implemented by hardware in the response unit 18 or by remote programming via a configuring unit similar to the configuring unit 28 shown in FIG. 2.

Further, the manufacturing process should include system verification and eventually calibration guidelines (for example, to position the antenna of the response unit 18 vertically). The unit 18 must be accessible with a very high probability and the read-out must be correct. This is especially important, when the unit 18 is used in combination with access or personal identification functions. Radio frequency signals tend to be sensitive to the way the device is built and to the placement orientation of critical components, in particular the radio frequency antenna.

In general, the unit 18 may be used not only as a signal response means for detecting the position of the hearing protection device into which the unit 18 is integrated, but it rather may also serve as an electromagnetic identification means integrated within the hearing protection device for enabling an individual identification of the hearing protection device—and hence of the user. In this case, the unit 18 has to provide for an identification signal which is individual to the respective hearing protection device.

Such personalized hearing protection device including identification means may serve, for example, to identify an operator using the hearing protection device, to provide for a contactless key to restricted areas or for controlling check-in/out times of operators.

Such a unit 18 serving as an electromagnetic identification means may be integrated not only into active or passive hearing protection devices but also into a hearing aid device, thus creating a personalized hearing aid device which may serve to identify the user wearing the hearing aid device, e.g. for the above-mentioned purposes.

In a further application the electromagnetic identification means integrated within a hearing protection device may serve to act as a tracer for determining the position of the hearing protection device when lost and no longer visible. This function is of particular interest, for example, in the food processing industry, where the processed food materials must be kept free from any foreign substances or articles. Therefore, there is a need to detect any lost articles in the processed food materials.

Figure 4:
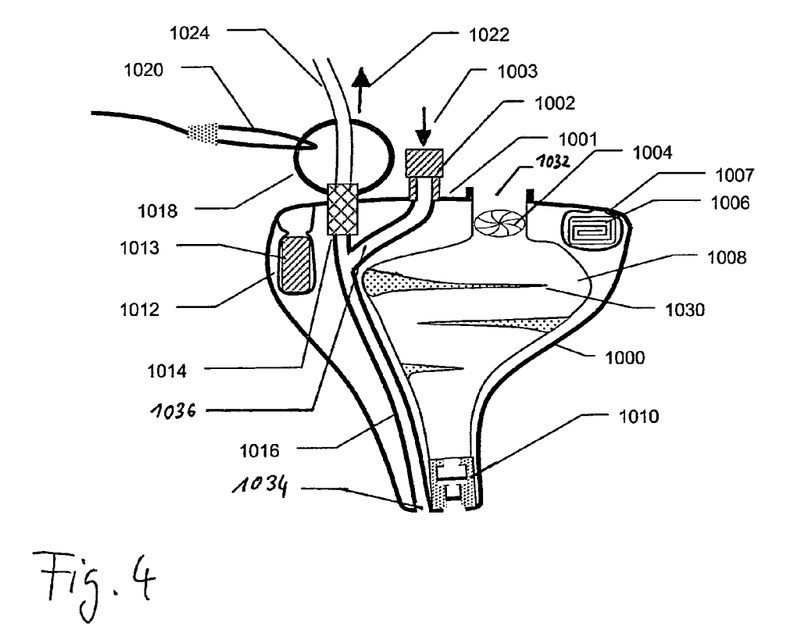
FIG. 4 shows a schematic longitudinal sectional view of an example of a passive hearing protection earplug according to the invention.
Figure 5:
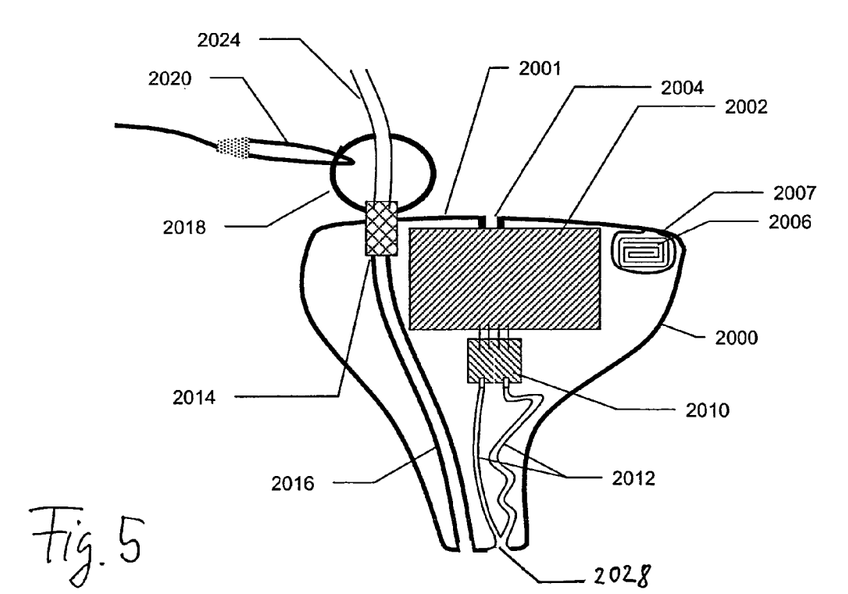
FIG. 5 shows a schematic longitudinal sectional view of an example of an active hearing protection earplug according to the invention.

FIGS. 4 and 5 show an example of a passive hearing protection earplug and an active hearing protection earplug, respectively, according to the present invention, wherein some features are combined which may be advantageously implemented by manufacturing the shell of the earplug by an additive build-up process, such as layer-by-layer laser sintering.

The basic idea is to use rapid prototyping technology in a manufacturing environment as described, for example, in U.S. Pat. No. 6,533,062 B1 or U.S. 2003/0133583 A1. This technique is successfully being used in hearing aids and can be applied in a similar fashion for HPDs. By doing this, a whole new range of features and functions become feasible for HPDs.

The key to the following features and functions is this technology's capability to model and customize the earplug both to fit the individual shape of the ear, but also to utilize the given shape and volume for additional functionality. In some cases the processed earplug (with the mentioned rapid prototyping technology) becomes the chassis for the additional function (e.g. "RFID (radio frequency identification)", "HPD detection part", "multipurpose cord adapter") or the function is fully integrated (e.g. "intelligent HPD resonator"). The following list of functions and features indicates examples of application.

The earplug of FIG. 4 includes a customized hard shell 1000 with a faceplate 1001 at its outer (proximal) end. The faceplate 1001 includes an outer sound input opening 1032 provided with a mechanical peak clipper 1004, a multipurpose cord adapter element 1014 with an in-situ measuring hole for optionally connecting the measuring hole to an external measuring tube 1024 or to a plug for closing the measuring hole in the normal operation of the earplug, and a sound inlet opening which is provided with a button 1002 which is manually operable in the direction 1003 to act as an attenuation button closing the sound inlet opening or as communication button opening the sound inlet opening for sound input into a sound passage 1036 which merges at its distal end with an in-situ measuring channel or tube 1016 which is acoustically connected to the measuring hole in adapter element 1014 and which extends to an inner sound opening 1034 at the inner end of the shell 1000. The sound input opening 1032 communicates with a resonance cavity 1008 with an inner mechanical structure 1030 for frequency tuning. At the distal end of the resonance cavity 1008 a semi-integrated passive acoustic filter 1010 is provided. The tubes 1036 and 1016 are formed integral with the shell 1000. Further, also an insert cavity 1007 for a RFID tag 1006 and an insert cavity 1012 for a detectable metal part 1013 are formed integral with the shell 1000. At the adapter element 1014 or at the plug for closing the measuring hole of the adapter element a cord fixation ring 1018 may be provided for fixing a neck cord 1020 at the shell 1000 for preventing loss of the earplug. The ring 1018 or the cord 1020 also may serve to manually pull the earplug in the axial direction 1022.

The earplug of FIG. 5 includes a customized hard shell 2000 with a faceplate 2001 at its outer end. The shell 2000 includes a cavity for an active unit 2002 which may comprises a microphone, an audio signal processing unit (e.g. an amplifier), a programming interface, a volume control, a push button and a battery. The unit 2002 produces an audio signal output for an output transducer unit 2010, comprising one or several speakers/receivers which are acoustically connected via sound output channels 2012 to a sound output opening 2028. The faceplate 2001 includes a faceplate opening 2004 which may serve for sound input to the microphone of the active unit 2002 and/or for access to the programming interface, the volume control, the push button and/or the battery of the active unit 2002. Similar to the passive HPD of FIG. 1, an internal in-situ measurement channel 2016 with an adapter element 2014 at the faceplate 2001 for temporarily connecting to an external measurement tube 2024, a cord fixation ring 2018, a neck cord 2020 and a cavity 2007 for a RFID-tag 2006 are provided.

The RFID-tags 1006, 2006 are provided for serving the functions described above in connection with FIGS. 1 to 3.

In the following, the features and functions of the earplugs of FIGS. 4 and 5 will be explained in more detail.

Multipurpose Cord Adapter

In order to confirm acoustical performance of an HPD, an in-situ measurement tube is implemented to allow measurement of attenuation when the individual wears the device. Naturally this tube needs to be closed off during normal operation. The core element of this tube is the faceplate component referred to a multipurpose cord adapter 1014, 2014 that embodies several functions and features: fixation of external in-situ measurement probe tube 1024, 2024, one possible holder of the cord fixation ring 1018, 2018 for the neck cord 1020, 2020, holder of an ergonomic pull means (e.g. the cord fixation ring 1018, 2018) for an inverse anatomy switch, holder of a plug for closing the in-situ tube during normal operation. If the element is made of metal it can serve as a metal component for detection purposes 1013 which in that case spares an extra insert cavity 1012. The design of the multipurpose cord adapter element 1014, 2014 is given extensive freedom (shape, material, insertion/removal concept, etc.) due to the base technology used for the faceplate portion of the earplug 1001, 2001.

Semi-Integrated Passive Filter

In passive HPDs acoustical filters mainly serve two purposes: firstly there is the defined amount of attenuation, secondly the filter can shape the frequency response of the attenuation in order to protect some frequencies while letting others through (e.g. block low frequency noise and let speech pass above 1 kHz). The proposed base technology enables both usages of predefined component placement geometries (e.g. cavities 1012 for metal component 1013 insertion) as well as semi-integration of functions where the material itself becomes part of the solution (e.g. insert cavities, acoustical filters). The semi-integrated passive filter 1010 is a structure of the second kind, where the tubes are made in shell material while the membranes are inserted components. Selection of membranes can be done to order and individual need, hence the component remains customizable. The filter must be considered and dimensioned together with other filter means like the customizable front chamber shaping structure (or resonance cavity) 1008, 1030 (Helmholtz resonator) and the mechanical peak clipper 1004.

Communication/Attenuation Button

A core function of a passive HPD is to enable temporary audio bypass for purposes like listening to speech, alarm or other desired audio signals even though they are mixed with loud noise. This is often performed by a push/return-button opening a tube either bypassing the filter of the system or leading into the in-situ measurement probe tube 1016 on the inside of the closing plug to be connected to the adapter element 1014 when the measuring tube 1024 is removed. The integration of such a device into the faceplate 1001 overcomes many drawbacks of similar standard component solutions (e.g. complex tubing, acoustical leakage). An even more integrated solution is achieved by building the switch directly into the multipurpose cord adapter core element 1014 replacing the sealing plug. If the button is made of metal it could serve as a metal piece for the detection function, thereby eliminating the need for the metal part 1013.

Inverse Anatomy Force Button

A further level of integration of the on/off switch is based on the shell technology combined with the natural anatomy of the outer ear. In addition to a defined audio "leak" via a tube 1016 through the HPD, there is the alternative of creating a temporary leak between the device and the outer ear by slightly pulling the device out of the ear. This pull can be done by the cord 1020 or directly by grip and pull on the cord ring 1018. If the shell 1000 is shaped in an appropriate manner, the ear shape is such that the device will be naturally pulled back in place when the pull is relaxed.

Intelligent Passive HPD

Inserting a device into the ear principally blocks the acoustical tube (ear canal) and destroys the natural outer ear amplification and frequency shaping (open ear gain, OEG). The open ear has a natural resonance in the frequency area of the most critical speech information, hence this loss is a real loss and not normally desired. The resonance frequency is given by the length of the tube; hence there is a need for compensation of the reduced length. This can be individually modeled and implemented with a defined acoustical front (outer) chamber 1008 and artificially stretched to a desired length by a mechanical means 1030 for resonance shaping directly integrated into the shell making process, possibly in combination with frequency shaping filter 1010 and means for maximum power limiting such as a mechanical peak clipper 1004.

Mechanical Peak Clipping

Many applications for HPDs experience strong variations in noise exposure over time. The extreme example is people shooting with guns (military, hunters) where speech communication in-between the actions is strongly desired and where the sound gets very loud for a short time. In active devices such conditions have been solved with so-called "peak clippers" which are fairly easy to implement in electronics and which limit the output of the device independent of the input signal while leaving the signal undistorted for normal noise levels. For a passive device this can be realized by a pressure sensitive valve 1004 opening or blocking the audio canal at the sound inlet.

Acoustical Tubing

Analog to the intelligent passive HPD acoustical shaping, several audio signal enhancements can be pursued by means of acoustical tubing for active HPD devices. Active HPDs are systems where the incoming sound picture is picked up by a transducer microphone system, processed electronically and converted back to acoustical domain by a transducer receiver (loudspeaker). Many properties and artifacts of the signal can be taken care of in the electronic domain, but some remain difficult (e.g. resonance peaks, relation direct (venting) and indirect (processed) sound) and in particular the upcoming challenge of managing wide band receivers (e.g. two-way) for high-fidelity applications. Broadband output transducers 2010 made for such applications produce multiple output signals the mixing of which becomes complex. The ability to determine the shape and length of the individual acoustic tubes 2012 and their mixing point becomes a design and modeling choice at production time. Naturally such a system can be combined with the semi-integrated passive filter mentioned earlier for further degrees of freedom.

Detectable HPD

HPDs are mostly used in industrial environments. In the food industry an additional requirement also affects these devices. Any foreign particle (to the food ingredients) must be detectable within the production process. For HPDs this implies that the devices need to contain a certain amount of metal to enable the detection equipment to find it if lost in the production line. Metal can be inserted into HPDs in a number of different ways: for active devices there should be enough metal in the transducers 2002, 2010 and the battery contained in 2002, hence no additional component is needed. In case of passive devices metal can be mixed into the shell base material 1000, a specific metal component 1013 can be mounted in a prepared cavity 1012, the cord adapter faceplate element 1014 can be made of metal and the button part of the on/off switch 1002 can be made of metal. In a HPD with a RFID tag, the tag itself is detectable if the equipment for detection is implemented in the production line.

Basic Functions

Functions that conventionally are mounted components, such as a grip handle for insertion and removal of the HPD, can easily be integrated with use of the shell technology. The product design and assembly more and more becomes a software issue and the individual product is increasingly designed to order according to the specific requirements of each customer.

While various embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as encompassed by the scope of the appended claims.

What is claimed is:

1. A system for monitoring use of a hearing protection unit comprising a left ear hearing protection device and a right ear hearing protection device to be worn by a user within a monitoring area, the system comprising: electronic means for wirelessly detecting a position of said left ear hearing protection device and a position of said right ear hearing protection device within said monitoring area, electronic means for judging whether a predefined condition for said detected positions of said left ear hearing protection device and said right ear hearing protection device is fulfilled, and means for outputting a wearing compliance signal depending on whether said predefined condition is found to be fulfilled by said judging means.

2. The system of claim 1, wherein said condition is at least one of that a vertical difference of said detected position of said left ear hearing protection device and said right ear hearing protection device is within a predefined range, that a vertical position of the said ear hearing protection device and a vertical position of said right ear hearing protection device are within a predefined range, that a mean of a vertical position of said left ear hearing protection device and said right ear hearing protection device is within a predefined range, and that a distance between said detected position of said left ear hearing protection device and said detected position of said right ear hearing protection device is within a predefined range.

3. The system of claim 2, wherein said condition is that a mean of said vertical position of said left ear hearing protection device and said right ear hearing protection device is within a predefined range and that a distance between said detected position of said left ear hearing protection device and said detected position of said right ear hearing protection device is within a predefined range.

4. The system of claim 1, further comprising means for converting said wearing compliance signal into at least one of an optical and an acoustic alarm signal, if said predefined condition is found to be not fulfilled.

5. The system of claim 1, further comprising means for determining when said user enters or said the monitoring area.

6. The system of claim 5, wherein said means for determining when said user enters or exits said monitoring area are adapted to determine when said user enters or exits said monitoring area by determining said positions of said hearing protection devices.

7. The system of claim 5, wherein said system is adapted to both detect said positions of said hearing protection devices and to output said wearing compliance signal over an entire period of time when said user is determined to be within said monitoring area.

8. The system of claim 1, further comprising means for determining when said user is at a predetermined location within said monitoring area.

9. The system of claim 8, wherein said means for determining when said user is at said predetermined location are adapted to determine when said user is at said predetermined location by determining the positions of said hearing protection devices.

10. The system of claim 8, wherein said system is adapted to both detect said positions of hearing protection devices and to output said wearing compliance signal at a time when said user is determined to be at said predetermined location.

11. The system of claim 1, wherein said detecting means comprise means for individually identifying said hearing protection devices from other hearing protection devices.

12. The system of claim 1, wherein said detecting means comprises means for transmitting/receiving electromagnetic signals located remote from said hearing protection devices and electromagnetic signal response means integrated within said hearing protection devices.

13. The system of claim 12, wherein said electromagnetic signal response means is adapted to produce, upon receipt of an electromagnetic input signal from said electromagnetic signal transmitting/receiving means, an electromagnetic response signal for said electromagnetic signal transmitting/receiving means.

14. The system of claim 13, wherein said electromagnetic response signal is different from said input signal.

15. The system of claim 13, wherein said electromagnetic signal response means is adapted to be energized by energy included in said input signal received from said electromagnetic signal transmitting/receiving means.

16. The system of claim 13, wherein said electromagnetic response signal is individually specific to each of said hearing protection devices.

17. The system of claim 16, further comprising means for individually configuring said electromagnetic signal response means in a wireless manner in order to individually define said response signal.

18. The system of claim 17, wherein said configuring means are implemented in a mobile device such as a personal computer, personal digital assistant or mobile phone.

19. The system of claim 13, wherein said electromagnetic signal response means comprise a non-volatile read/write data memory.

20. The system of claim 13, wherein said electromagnetic signal response means further comprises an antenna, an analog circuit for receiving and transmitting radio frequency signals, a digital circuit and a non-volatile data memory.

21. The system of claim 13, wherein said electromagnetic signal response means comprises an antenna, an analog circuit for receiving and transmitting radio frequency signals and a surface acoustic wave device.

22. The system of claim 13, wherein said electromagnetic signal transmitting/receiving means and said electromagnetic signal response means are adapted to be coupled inductively in order to have said electromagnetic signal response means produce said response signal.

23. The system of claim 13, wherein said signal response means is adapted for modulated reflection of said input signal in order to produce said response signal.

24. The system of claim 12, wherein said electromagnetic signal response means is inserted in a cavity of each of said hearing protection devices.

25. The system of claim 12, wherein said means for transmitting/receiving electromagnetic signals and said electromagnetic signal response means are adapted to operate at radio frequencies.

26. The system of claim 25, wherein said electromagnetic signal response means is a radio frequency identification tag.

27. The system of claim 1, wherein each of said hearing protection devices is an earplug and includes a hard shell having an outer surface individually shaped according a measured inner shape of said user's ear canal and outer ear.

28. The system of claim 27, wherein said cavity for said electromagnetic signal response means is formed within said hard shell.

29. A method for monitoring a use of a hearing protection unit comprising a left ear hearing protection device and a right ear hearing protection device to be worn by a user within a monitoring area, comprising: electronically detecting a position of said left ear hearing protection device and a position of said right ear hearing protection device within said monitoring area, electronically judging whether a predefined condition for said detected positions of said left ear hearing protection device and said right ear hearing protection device is fulfilled, and outputting a wearing compliance signal depending on whether said predefined condition is found to be fulfilled.

30. The method of claim 20, wherein said wearing compliance signal is converted into at least one of an optical and an acoustic alarm signal, if said predefined condition is found to be not fulfilled.

* * * * *